United States Patent
Meadows

(10) Patent No.: US 7,783,359 B2
(45) Date of Patent: *Aug. 24, 2010

(54) DEVICES AND METHODS USING AN IMPLANTABLE PULSE GENERATOR FOR BRAIN STIMULATION

(75) Inventor: Paul Milton Meadows, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 1003 days.

This patent is subject to a terminal disclaimer.

(21) Appl. No.: 11/230,052

(22) Filed: Sep. 19, 2005

(65) Prior Publication Data
US 2006/0149336 A1    Jul. 6, 2006

Related U.S. Application Data

(63) Continuation-in-part of application No. 11/030,546, filed on Jan. 5, 2005.

(51) Int. Cl.
*A61N 1/36* (2006.01)
(52) U.S. Cl. .......................... 607/45; 607/115
(58) Field of Classification Search ............... 607/48, 607/45, 46, 115, 116, 117
See application file for complete search history.

(56) References Cited

U.S. PATENT DOCUMENTS

| | | | |
|---|---|---|---|
| 4,350,159 A | 9/1982 | Gouda | |
| 4,471,777 A | 9/1984 | McCorkle, Jr. | |
| 4,565,200 A | 1/1986 | Cosman | |
| 4,668,221 A * | 5/1987 | Luther | 604/164.03 |
| 4,886,065 A | 12/1989 | Collins, Jr. | |
| 4,931,056 A | 6/1990 | Ghajar et al. | |
| 4,955,891 A | 9/1990 | Carol et al. | |
| 5,006,122 A | 4/1991 | Wyatt et al. | |
| 5,114,424 A * | 5/1992 | Hagen et al. | 606/32 |
| 5,116,345 A | 5/1992 | Jewell et al. | |
| 5,300,080 A | 4/1994 | Clayman et al. | |
| 5,303,704 A * | 4/1994 | Molacek et al. | 600/377 |
| 5,318,041 A | 6/1994 | DuBois et al. | |

(Continued)

FOREIGN PATENT DOCUMENTS

EP    1062973 A1    12/2000

(Continued)

OTHER PUBLICATIONS

"System and Method for Selective Multi-site Microelectrode Recording", IP.com, IPCOM00001 6587D, Jul. 1, 2003.

(Continued)

*Primary Examiner*—Carl H Layno
*Assistant Examiner*—Brian T Gedeon
(74) *Attorney, Agent, or Firm*—Frommer Lawrence & Haug LLP; Bruce E. Black

(57) ABSTRACT

A device for brain stimulation includes a lead having a longitudinal surface; at least one stimulation electrode disposed along the longitudinal surface of the lead; at least one recording electrode, separate from the at least one stimulation electrode, disposed on the lead; and an implantable pulse generator coupled to the at least one stimulation electrode. In some instances, the implantable pulse generator can be implanted into a burr hole in the skull made for insertion of the lead into the brain.

21 Claims, 6 Drawing Sheets

U.S. PATENT DOCUMENTS

| | | | |
|---|---|---|---|
| 5,330,485 A | | 7/1994 | Clayman et al. |
| 5,450,846 A | * | 9/1995 | Goldreyer ............... 600/374 |
| 5,618,287 A | | 4/1997 | Fogarty et al. |
| 5,728,148 A | * | 3/1998 | Bostrom et al. ............ 607/116 |
| 5,752,937 A | | 5/1998 | Otten et al. |
| 5,843,148 A | * | 12/1998 | Gijsbers et al. ............ 607/116 |
| 5,913,882 A | * | 6/1999 | King ........................ 607/62 |
| 5,925,073 A | | 7/1999 | Chastain et al. |
| 5,978,713 A | * | 11/1999 | Prutchi et al. ............... 607/60 |
| 6,011,996 A | | 1/2000 | Gielen et al. |
| 6,026,567 A | | 2/2000 | Swoyer et al. |
| 6,066,165 A | | 5/2000 | Racz |
| 6,181,971 B1 | | 1/2001 | Doan |
| 6,261,300 B1 | | 7/2001 | Carol et al. |
| 6,301,492 B1 | | 10/2001 | Zonensheyn |
| 6,343,226 B1 | | 1/2002 | Sunde et al. |
| 6,413,263 B1 | | 7/2002 | Lobdill et al. |
| 6,416,520 B1 | | 7/2002 | Kynast et al. |
| 6,456,869 B1 | | 7/2002 | Raylman et al. |
| 6,456,889 B2 | | 9/2002 | Pianca et al. |
| 6,529,774 B1 | * | 3/2003 | Greene ..................... 600/545 |
| 6,572,624 B2 | | 6/2003 | U et al. |
| 6,597,954 B1 | * | 7/2003 | Fischell et al. ............... 607/62 |
| 6,687,549 B1 | * | 2/2004 | Helland et al. ............. 607/122 |
| 6,782,292 B2 | * | 8/2004 | Whitehurst ................. 607/45 |
| 6,849,062 B2 | * | 2/2005 | Kantor ................. 604/103.04 |
| 7,177,701 B1 | * | 2/2007 | Pianca ..................... 607/116 |
| 7,212,867 B2 | * | 5/2007 | Van Venrooij et al. ....... 607/116 |
| 2001/0027336 A1 | | 10/2001 | Gielen et al. |
| 2002/0151924 A1 | * | 10/2002 | Shiber ...................... 606/194 |
| 2002/0183817 A1 | * | 12/2002 | Van Venrooij et al. ....... 607/116 |
| 2004/0199235 A1 | * | 10/2004 | Younis ..................... 607/116 |
| 2005/0004637 A1 | * | 1/2005 | Singhal et al. ............. 607/116 |
| 2005/0015130 A1 | * | 1/2005 | Gill .......................... 607/116 |
| 2008/0103572 A1 | * | 5/2008 | Gerber ..................... 607/116 |

FOREIGN PATENT DOCUMENTS

| | | |
|---|---|---|
| WO | WO-99/36122 A1 | 7/1999 |

OTHER PUBLICATIONS

"Universal Instrument Guide and Surgical Insertion Tool for Stereotactic Frames", IP.com. IPCOM000011023D, Feb. 7, 2003.

Pianca, et al.; U.S. Appl. No. 10/035,745, filed Dec. 28, 2001; entitled "Systems and Methods of Implanting a Lead for Brain Stimulation".

Pianca; U.S. Appl. No. 10/459,068, filed Jun. 11, 2003; entitled "System for Permanent Electrode Placement Utilizing Microelectrode Recording Methods".

U.S. Appl. No. 11/030,546 Official Communication Mailed Sep. 26, 2007.

U.S. Appl. No. 11/030,546 Official Communication Mailed Mar. 20, 2008.

U.S. Appl. No. 11/030,546 Official Communication Mailed May 21, 2008.

U.S. Appl. No. 11/030,546 Official Communication Mailed Jan. 21, 2009.

U.S. Appl. No. 11/030,546 Official Communication Mailed May 22, 2009.

U.S. Appl. No. 11/030,546 Official Communication Mailed Dec. 7, 2009.

U.S. Appl. No. 11/030,546 Official Communication Mailed Dec. 28, 2009.

* cited by examiner

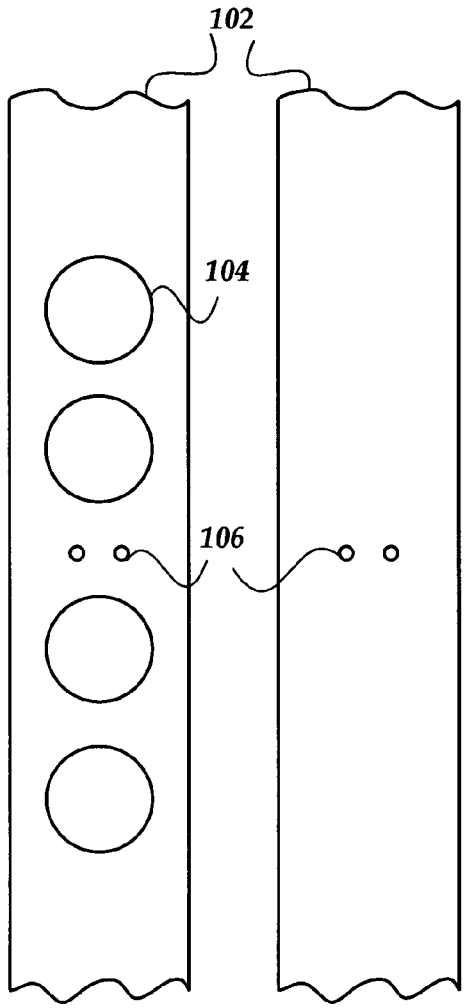
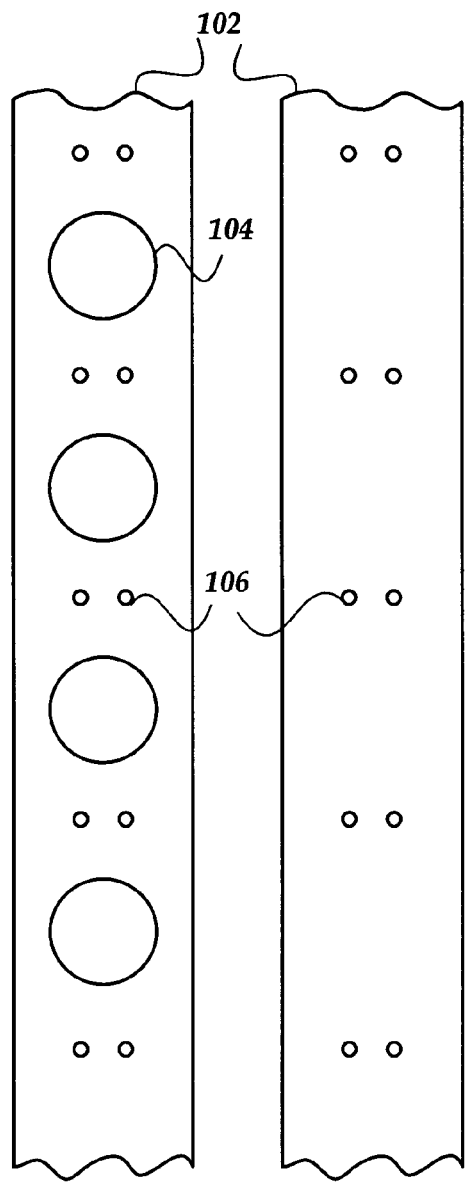
Figure 2A    Figure 2B
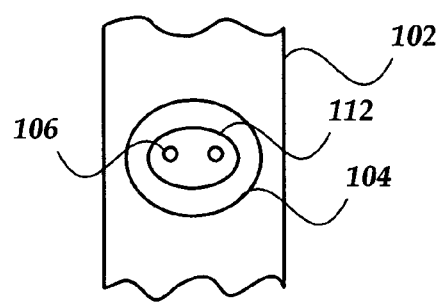
Figure 4
Figure 3A    Figure 3B

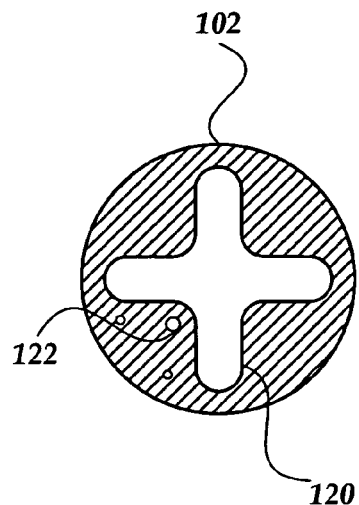
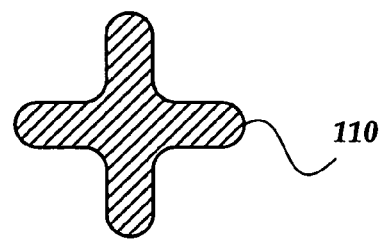
Figure 5A        Figure 5B
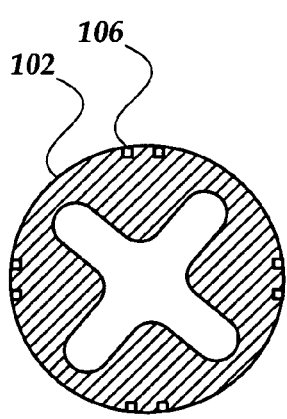
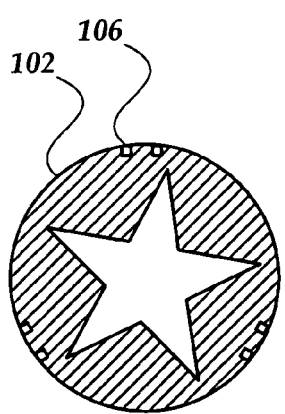
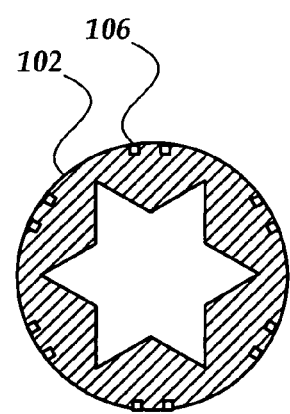
Figure 6A        Figure 6B        Figure 6C

DEVICES AND METHODS USING AN IMPLANTABLE PULSE GENERATOR FOR BRAIN STIMULATION This application is a continuation-in-part of U.S. patent application Ser. No. 11/030,546, filed Jan. 5, 2005, incorporated herein by reference.

FIELD

The invention is directed to devices and methods for brain stimulation including deep brain stimulation. In addition, the invention is directed to devices and method for brain stimulation using a lead with at least one stimulating electrode and an implantable pulse generator.

BACKGROUND

Deep brain stimulation can be useful for treating a variety of conditions including, for example, Parkinson's disease, dystonia, essential tremor, chronic pain, Huntington's Disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging (MRI) or computerized tomography (CT) scans can provide a starting point for determining where the stimulating electrode should be positioned to provide the desired stimulus to the target neurons. To further refine the position, a recording lead with a recording electrode at or near the tip of the recording lead can be inserted into the brain of the patient to determine a more precise location. Typically, the recording lead is guided to the target location within the brain using a stereotactic frame and microdrive motor system.

As the recording lead is moved through the brain, the recording electrode is observed to determine when the recording electrode is near the target neurons. This observation may include activating the target neurons to generate electrical signals that can be received by the recording electrode. Once the position of the target neurons is determined, the recording lead can be removed and the stimulating lead inserted. The object of this removal of the recording lead and insertion of the stimulating lead is to attempt to precisely locate the target neurons. The precise insertion of the stimulating lead and positioning of the stimulating lead in the precise location indicated by the recording lead can be particularly difficult. In some instances, multiple insertions of the recording lead and stimulating lead may need to occur to properly position the stimulating electrode.

BRIEF SUMMARY

One embodiment is a device for brain stimulation that includes a lead having a longitudinal surface; at least one stimulation electrode disposed along the longitudinal surface of the lead; and at least one recording electrode, separate from the at least one stimulation electrode, disposed along the longitudinal surface of the lead.

Another embodiment is a device for brain stimulation that includes a lead having a circumference; and a set of recording electrodes disposed at intervals around the circumference of the lead.

Yet another embodiment is a device for brain stimulation that includes a lead defining a lumen having a non-circular lateral cross-section; and at least one electrode disposed on the lead.

A further embodiment is a method for brain stimulation. A lead is inserted into a cranium of a patient. The lead includes at least one stimulation electrode disposed along a longitudinal surface of the lead; and at least one recording electrode, separate from the at least one stimulation electrode, disposed along the longitudinal surface of the lead. Target neurons are identified using the at least one recording electrode. The target neurons are stimulated using the at least one stimulation electrode.

Another embodiment is a device for brain stimulation. The device includes a lead having a longitudinal surface; at least one stimulation electrode disposed along the longitudinal surface of the lead; at least one recording electrode, separate from the at least one stimulation electrode, disposed on the lead; and an implantable pulse generator coupled to the at least one stimulation electrode. In some instances, the implantable pulse generator can be implanted into a burr hole in the skull made for insertion of the lead into the brain.

Yet another embodiment is a method for brain stimulation. A lead is inserted into a cranium of a patient. The lead includes at least one stimulation electrode disposed along a longitudinal surface of the lead; and at least one-recording electrode, separate from the at least one stimulation electrode, disposed on the lead. Target neurons are identified using the at least one recording electrode. A pulse generator is implanted in the patient. The target neurons are stimulated using the at least one stimulation electrode and the implanted pulse generator.

A further embodiment is a device for brain stimulation. The device includes a lead having a longitudinal surface; at least one stimulation electrode disposed along the longitudinal surface of the lead; an implantable pulse generator coupled to the at least one stimulation electrode and comprising a receiver; and an external control unit comprising a transmitter to transmit signals to the implantable pulse generator.

Another embodiment is a device for brain stimulation. The device includes a lead having a longitudinal surface; at least one stimulation electrode disposed along the longitudinal surface of the lead; an implantable pulse generator coupled to the at least one stimulation electrode and comprising a transmitter; and an external control unit comprising a receiver to receive signals from the implantable pulse generator.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 2A is a schematic side view of one embodiment of an electrode configuration for use with the lead of FIG. 1, according to the invention;

FIG. 2B is a schematic side view of one embodiment of an opposite side of the lead illustrated in FIG. 2A, according to the invention;

FIG. 3A is a schematic side view of another embodiment of an electrode configuration for use with the lead of FIG. 1, according to the invention;

FIG. 3B is a schematic side view of one embodiment of an opposite side of the lead illustrated in FIG. 3A, according to the invention;

FIG. 4 is a schematic side view of one embodiment of a recording electrode and stimulation electrode arrangement, according to the invention;

FIG. 5A is a schematic cross-sectional view of one embodiment of a lead with a cross lumen, according to the invention;

FIG. 5B is a schematic cross-sectional view of one embodiment of a stylet for use with the lead of FIG. 5A, according to the invention;

FIGS. 6A, 6B, and 6C are schematic cross-sectional views of three embodiments illustrating recording electrode arrangements arranged around the circumference of a lead, according to the invention;

DETAILED DESCRIPTION

The present invention is directed to the area of devices and methods for brain stimulation including deep brain stimulation. In addition, the invention is directed to devices and methods for brain stimulation using a lead with at least one recording electrode and at least one stimulating electrode. In addition, the invention is directed to devices and methods for brain stimulation using a lead with at least one stimulating electrode and an implantable pulse generator.

A lead for deep brain stimulation can include both recording and stimulation electrodes. This allows a practitioner to determine the position of the target neurons using the recording electrode(s) and then position the stimulation electrode(s) accordingly without removal of a recording lead and insertion of a stimulation lead. A lead can also include recording electrodes spaced around the circumference of the lead to more precisely determine the position of the target neurons. In at least some embodiments, the lead is rotatable so that the stimulation electrodes can be aligned with the target neurons after the neurons have been located using the recording electrodes.

Figure 1:
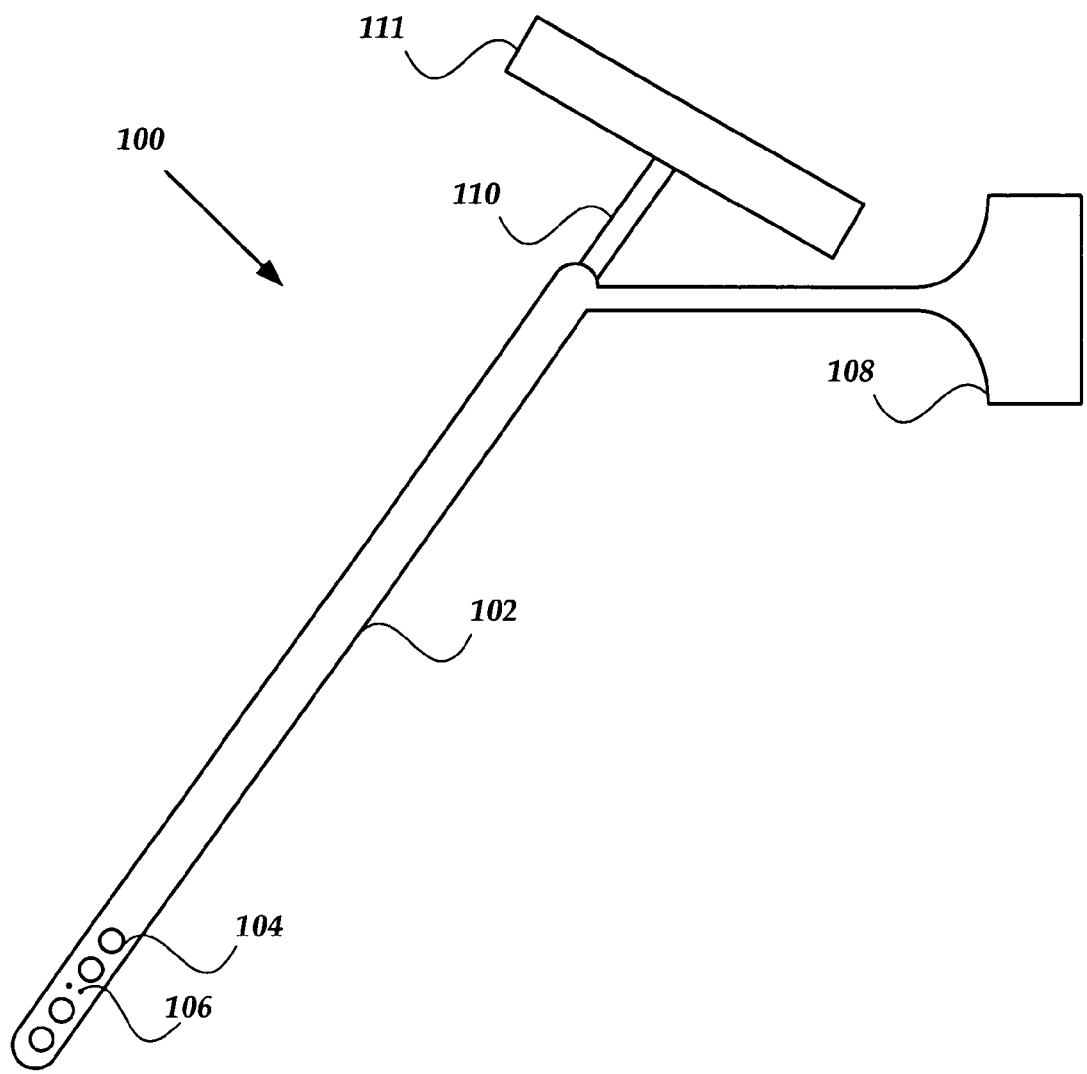
FIG. 1 is a schematic side view of one embodiment of a lead and stylet, according to the invention.

FIG. 1 illustrates one embodiment of a device 100 for brain stimulation. The device includes a lead 102, one or more stimulation electrodes 104, one or more recording electrodes 106, a connector 108 for connection of the electrodes to a control unit, and a stylet 110 for assisting in insertion and positioning of the lead in the patient's brain.

The lead 102 can be formed of a non-conducting material such as, for example, a polymeric material. Suitable polymeric materials include, for example, silicone rubber and polyethylene. Preferably, the lead is made using a biocompatible material. In at least some instances, the lead may be in contact with body tissue for extended periods of time.

The lead often has a cross-sectional diameter of no more than 1.5 mm and may be in the range of 0.7 to 1.3 mm. The lead often has a length of at least 10 cm and the length of the lead may be in the range of 30 to 70 cm.

The lead typically defines a lumen 120 (see FIG. 5A) within the lead for the removable stylet 110. Use of a stylet can facilitate insertion of the lead into the cranium and brain tissue and facilitate positioning the lead to stimulate the target neurons. The stylet can provide rigidity to the lead during the insertion process.

The lumen can have any shape. In one embodiment, the lateral cross-sectional shape of the lumen is non-circular. For example, the lateral cross-sectional shape of the lumen can have an oval, square, rectangular, or, as illustrated in FIG. 5A, a cross shape. The stylet 110 will typically have a corresponding lateral cross-sectional shape. For example, a stylet 110 may have a cross shape as illustrated in FIG. 5B for use with the lead illustrated in FIG. 5A. The non-circular lateral cross-sectional shape can permit the practitioner to rotate the lead 102 by rotating the stylet 110. Because the lumen is non-circular, the stylet can not rotate within the lead and, therefore, rotation of the stylet results in rotation of the lead. A cross shaped lumen can be particularly useful, as opposed to an oval, square or rectangular lumen, if the shape of the lumen might be deformed by rotation of the stylet because the lead is not sufficiently rigid. Shapes similar to cross, with multiple arms extending from a central cavity, such as an asterisk- or star-shaped lumen (see FIGS. 6B and 6C) and corresponding stylet, can be similarly useful.

The stylet 110 can be made of a rigid material. Examples of suitable materials include tungsten, stainless steel, or plastic. The stylet 110 may have a handle 111 to assist insertion into the lead, as well as rotation of the stylet and lead.

Conductors 122 (e.g., wires) that attach to or form the recording electrode(s) 106 and stimulation electrode(s) 104 also pass through the lead 102. These conductors may pass through the material of the lead as illustrated, for example, in one configuration for FIG. 5A, or through the lumen 120 or through a second lumen defined by the lead. The conductors 122 are presented at the connector 108 for coupling of the electrodes 104, 106 to a control unit (not shown). The control unit observes and records signals from the recording electrodes 106. The same or a different control unit can also be used to provide stimulation signals, often in the form of pulses, to the stimulation electrodes 104.

The lead 102 includes one or more recording electrodes 106 disposed along the longitudinal axis of the lead near a distal end of the lead. In at least some embodiments, the lead includes a plurality of recording electrodes. The recording electrodes can be made using a metal, alloy, conductive oxide, or other conductive material. Examples of suitable materials include platinum, iridium, platinum iridium alloy, stainless steel, titanium, or tungsten.

Any type of recording electrode can be used including monopolar recording electrodes, bipolar recording electrodes (as illustrated in FIGS. 1-4), and other multipolar recording electrodes. In at least some embodiments, bipolar or other multipolar recording electrodes are preferred because they can assist in finding nearby electrical signals, and disregard distant electrical signals, by observation of the differential between the signals from the two or more, closely-spaced electrodes.

Any type of recording electrode can be used including electrode pads or plates. A preferred recording electrode for at least some embodiments is a tip of a wire. This type of electrode can assist in more precise location of the target neurons because of the small surface area and high impedance for detection of electrical signals. Such recording electrodes often have a diameter of no more than 100 µm or no more than 25 µm. The diameter may be in the range from, for example, 25 µm to 100 µm. In one embodiment, the recording electrodes 106 correspond to wire conductors 122 that extend out of the lead 102 and are then trimmed or ground down flush with the lead surface.

The lead 102 also includes one or more stimulation electrodes 104 arranged along the longitudinal axis of the lead near a distal end of the lead. In at least some embodiments, the lead includes a plurality of stimulation electrodes. A conductor 122 is attached to each stimulation electrode 104. The stimulation electrodes often have a surface area of at least 1 mm$^2$ or at least 5 mm$^2$. The surface area may be in the range from, for example, 1 mm$^2$ to 6 mm$^2$. A variety of shapes can be used for the stimulation electrodes including, for example, rings, circles, ovals, squares, rectangles, triangles, etc. In some embodiments, a stimulation electrode 104 forms a ring that fully or substantially encircles the lead 102. Preferably, however, the stimulation electrodes are not rings, but are instead discrete shapes disposed on one side of the lead. Ring electrodes typically stimulate neurons on all sides of the lead instead of focusing on the target neurons that may face only a portion of the lead circumference.

The stimulation electrodes can be made using a metal, alloy, conductive oxide or other conductive material. Examples of suitable materials include platinum, iridium, platinum iridium alloy, stainless steel, titanium, or tungsten. Preferably, the stimulation electrodes are made of a material that is biocompatible and does not substantially corrode under expected operating conditions in the operating environment for the expected duration of use.

The arrangement of recording electrodes 106 and stimulation electrodes 104 on the lead 102 can facilitate detection and stimulation of target neurons. Some embodiments include a single recording electrode and a single stimulation electrode. Other embodiments, however, include two or more recording electrodes, two or more stimulation electrodes, or both.

FIG. 2A illustrates one embodiment of an electrode arrangement along the lead 102. In this embodiment, there are a plurality of stimulation electrodes 104 aligned along one side of the lead with a recording electrode 106 positioned in the center of the arrangement. In other embodiments, the recording electrode 106 can be positioned in any relationship relative to the array of stimulation electrodes including, for example, below or above all of the stimulation electrodes or between any two of the stimulation electrodes. When the target neurons have been discovered using the recording electrode, they can be stimulated using one or more of the stimulation electrodes. Optionally, the lead can be advanced or retreated to further align one or more of the stimulation electrodes with the target neurons.

FIG. 3A illustrates another embodiment of an electrode arrangement. In this arrangement, recording electrodes 106 are provided above and below each stimulation electrode 104 in an array of stimulation electrodes. Again, variations on this arrangement can be made. For example, recording electrodes may only be provided above and below, but not between, the array of stimulation electrodes. In another arrangement, the recording electrodes may be positioned only between the stimulation electrodes or only positioned between selected stimulation electrodes but not between others.

In other embodiments, one or more recording electrodes 106 may be provided within one or more of the stimulation electrodes 104. One example of such an arrangement is illustrated in FIG. 4. In this arrangement, the stimulation electrode 104 surrounds the recording electrode 106. There is a non-conducting region 112 separating the stimulation electrode 104 and the recording electrode 106. This electrode arrangement may be advantageous when the recording electrode identifies the target neurons because the stimulation electrode is already in place to stimulate the target neurons. In addition, during operation of the lead, the recording electrodes can be periodically checked to determine whether the lead is still correctly positioned to stimulate the target neurons without needing to move the lead to align the recording electrodes with the target neurons. In these embodiments, recording electrode(s) can be positioned within each stimulation electrode or within a select number of stimulation electrodes or even within only one of the stimulation electrodes.

In at least some embodiments, recording electrodes 106 are arranged at various positions around the lateral circumference of the lead 102. Examples of such arrangements are illustrated in the cross-sectional views of FIGS. 6A, 6B, and 6C. In these arrangements, the recording electrodes are positioned in irregular or, preferably, regular intervals around the lead. For example, in FIG. 6A, the recording electrodes 106 are positioned around the lead with about 90° separation between neighboring recording electrodes. In FIG. 6B, the recording electrodes 106 are positioned around the lead with about 120° separation between neighboring recording electrodes. In FIG. 6C, the recording electrodes 106 are positioned around the lead with about 60° separation between neighboring recording electrodes. It will be recognized that other arrangements can be made including, for example, arrangements with 180° or 72° separation between recording electrodes 106.

In yet another embodiment, a recording electrode can be placed at a tip of the lead 102. This can be the sole recording electrode of the lead or additional recording electrodes can be placed at one or more positions away from the tip of the lead, as described above.

Positioning the recording electrodes 106 around the lead 102 in this manner can assist in determining the position of the target neurons because the recording electrodes can sample the brain tissue around the lead without rotating the lead. FIGS. 2B and 3B illustrate embodiments with recording electrodes 106 on the opposite side of the lead from the stimulation/recording electrode arrangements illustrated in FIGS. 2A and 3A, respectively.

Stimulation electrodes 104 can be positioned around the circumference of the lead 102 in a similar manner as that described for the recording electrodes. In at least some embodiments, however, stimulation electrode(s) 104 are positioned only along one side of the lead 102 and one or more sets of recording electrodes 106 are arrayed around the lateral circumference of the lead. Sets of recording electrodes can be displaced from each other longitudinally along the lead (e.g., the arrangement illustrated in FIGS. 3A and 3B). Optionally, one or more of the recording electrodes can be positioned within one or more of the stimulation electrode using an arrangement such as that illustrated in FIG. 4.

The recording electrodes 106 can be used to determine the site of the target neurons and then the lead can then be rotated, if necessary when the recording electrode is not one of those aligned with the stimulation electrode(s), and advanced or retreated, if necessary or desired, to align the stimulation electrode(s) with the target neurons. Rotation of the lead can be facilitated using a stylet and lead with non-circular lumen such as, for example, those illustrated in FIGS. 5A and 5B. The stylet or the proximal end of the lead may include an alignment marker to indicate where stimulation electrodes are provided along the lead.

Figure 7:
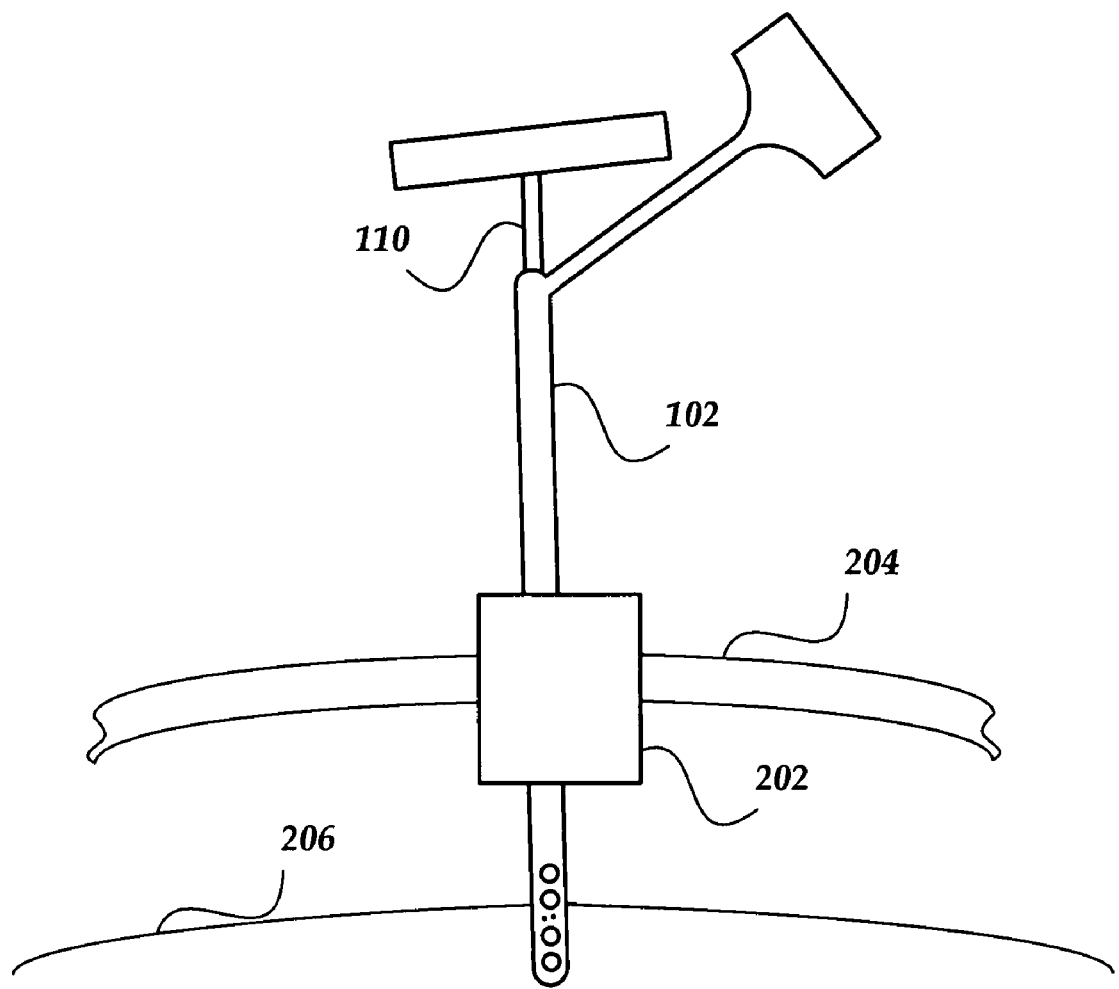
FIG. 7 is a schematic side view of a lead and associated hardware for insertion into a cranium, according to the invention.

In one example of operation of the lead illustrated in FIG. 7, access to the desired position in the brain can be accomplished by drilling a hole in the patient's skull or cranium 206 with a cranial drill (commonly referred to as a burr), and coagulating and incising the dura mater, or brain covering. The lead 102 can be inserted into the cranium and brain tissue with the assistance of the stylet 110. The lead can be guided to the target location within the brain using, for example, a stereotactic frame 204 and a microdrive motor system 202. The recording electrode(s) 106 can be observed using a control unit (not shown) attached to the conductors 122 exposed at the connector 108 to identify the target neurons. Once identified, the lead can be rotated, if necessary, and advanced or retreated, if necessary, to align the stimulation electrode(s) with the target neurons. The stimulation electrodes can then be activated to provide the desired stimulation to the target neurons and the stylet can then be removed.

In some embodiments, the microdrive motor system 202 can be fully or partially automatic. For example, the microdrive motor system 202 can perform one or more actions on the lead 102 in response to the signals from the recording electrode(s) 106, stimulation electrode(s) 104, or both. The microdrive motor system may be configured to perform one or more the following actions (alone or in combination): rotate the lead, insert the lead, or retract the lead. In one embodiment, the microdrive motor system can rotate the lead to position the stimulation electrode(s) in the position of the recording electrode(s) that detect the target neurons. In another embodiment, the microdrive motor system can rotate the lead partially and the recording electrode(s) can then be observed in the new position to iteratively determine the best position for the stimulation electrode(s). For example, if recording electrodes are positioned every 90° around the lead, the initial rotation of the lead can be less than 90° (e.g., 30° or 45°) and the recording electrodes can again be observed to more accurately identify the location of the target neurons.

In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

Figure 8:
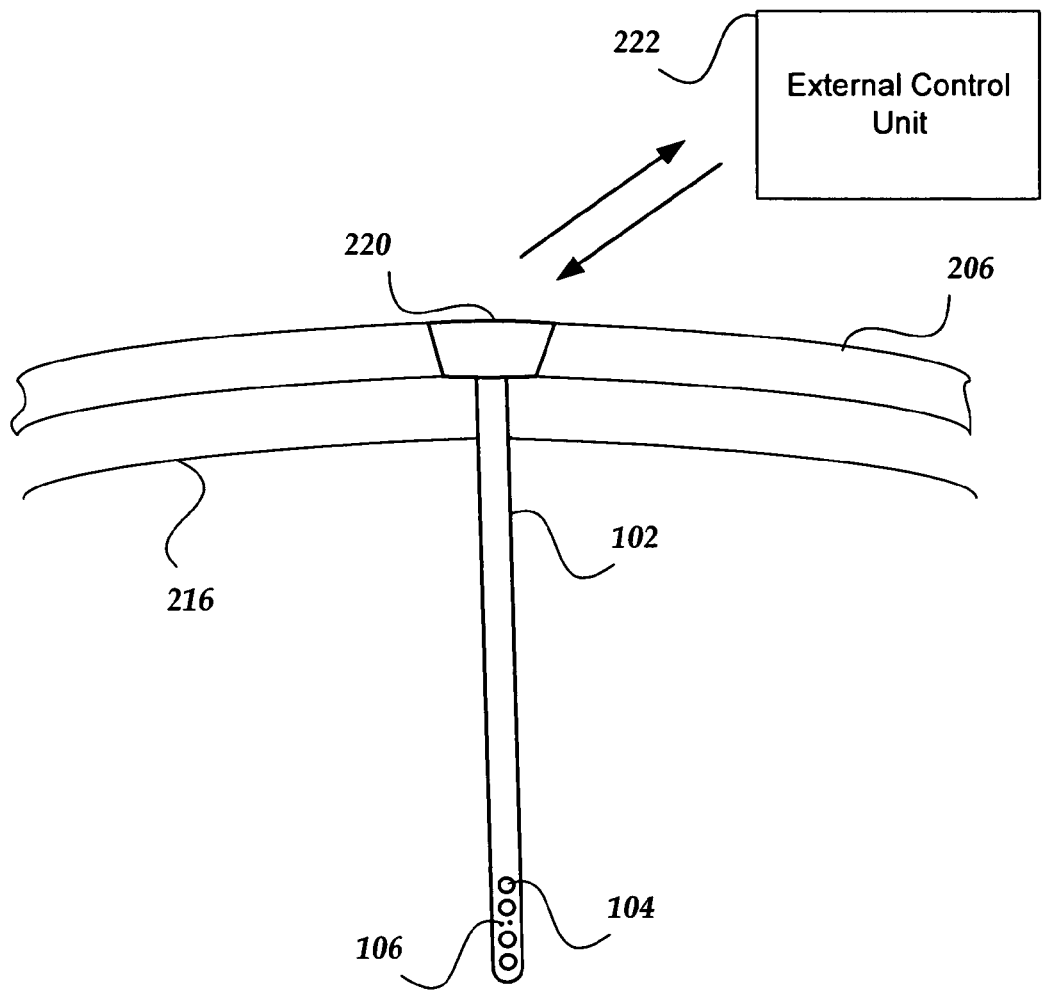
FIG. 8 is a schematic side view of one embodiment of a lead with an implantable pulse generator unit, according to the invention.

FIG. 8 illustrates another embodiment that includes a lead 102 and an implantable pulse generator unit 220 coupled to the lead. The lead 102 includes one or more stimulation electrodes 104 and, optionally, one or more recording electrodes 106. The arrangement of these electrodes can be selected as described above. The stimulation electrode(s) 104 and, optionally, any recording electrodes 106, are coupled to the implantable pulse generator unit 220 by conductors running through the lead 102.

The implantable pulse generator unit 220 can be permanently or detachably coupled to the lead 102. In some embodiments, the lead 102 has a connector (not shown) that can be coupled to the implantable pulse generator unit 220 before, during, or after implantation of the lead into the brain tissue 216. In one embodiment, the lead 102 is implanted as illustrated and discussed relative to FIG. 7. The implantable pulse generator is then coupled to the lead after implantation. In another embodiment, the implantable pulse generator is coupled to the lead during implantation and the implantable pulse generator provides signals from the recording electrodes to an external control unit to determine the tissue to be stimulated. Once the lead is implanted and positioned, the implantable pulse generator is implanted.

The implantable pulse generator can be implanted in any convenient portion of the body including in the neck or behind the ear. In one embodiment, the implantable pulse generator is implanted in the burr hole in the patient's skull 206 formed for insertion of the lead 102. Preferably, the implantable pulse generator does not extend substantially outside the exterior of the skull. Preferably, the implantable pulse generator is adhesively attached to the skull and/or a plate is positioned over the burr hole and attached to the skull or scalp to keep the implantable pulse generator in place. Preferably, the implantable pulse generator does not extend too far into the cranial cavity so that contact with brain tissue is avoided.

The implantable pulse generator unit 220 provides pulses of electrical energy to the stimulation electrode(s) 104 to stimulate the desired brain tissue. In some embodiments, the implantable pulse generator unit can also perform one or more other functions such as, for example, receiving signals from the recording electrodes; evaluating signals from the recording electrodes; altering or adjusting stimulation pulse parameters such as, for example, pulse frequency, pulse duration, pulse waveform, and pulse strength, as well as determine which electrodes receive the pulse; transmitting information to an external control unit 222; receiving signals, such as control signals or information, from an external control unit 222; and controlling or signaling other implant systems such as pumps.

Figure 9:
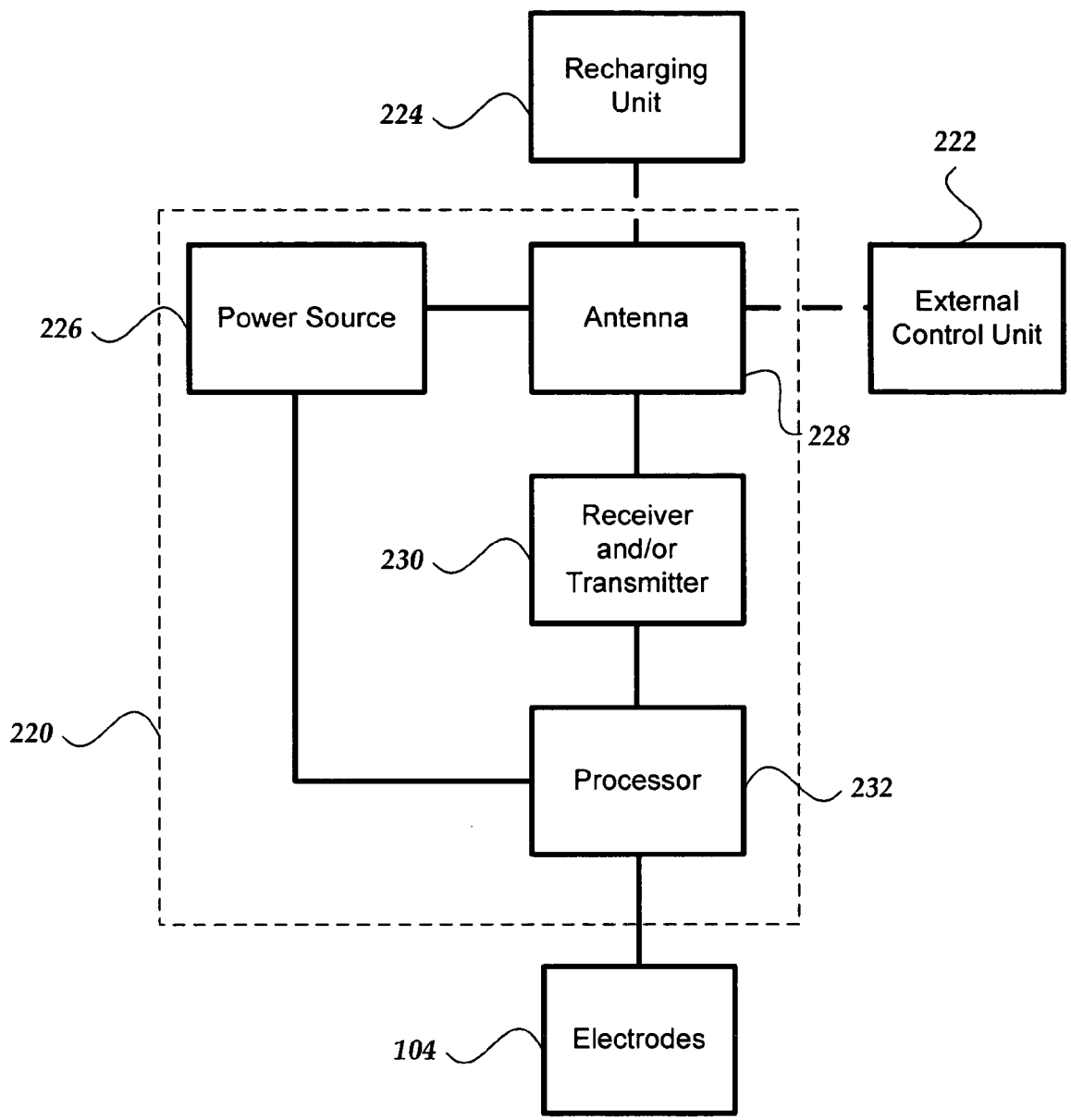
FIG. 9 is a schematic block diagram of one embodiment of an implantable pulse generator unit, according to the invention.

The implantable pulse generator can include a power source 226, as illustrated in FIG. 9. Any power source can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via an optional antenna 228. The external power source can be in a device that is mounted on the skin of the user or in a unit that is provided near the patient on a permanent or periodic basis.

If the power source 226 is a rechargeable battery, the battery may be recharged using the optional antenna 228, if desired. Power can be provided to the battery 226 for recharging by inductively coupling the battery through the antenna to a recharging unit 224 external to the patient.

A processor 232 is typically provided in the implantable pulse generator to control the timing and electrical characteristics of the pulses sent to the electrodes. For example, the processor can, if desired, control one or more of the timing, periodicity, strength, duration, and waveform of the pulses. Any processor can be used and can be as simple as a electronic device that produces pulses at a regular interval or the processor can be capable of receiving and interpreting instructions from an external control unit 222.

In one embodiment, the antenna 228 is capable of receiving signals (e.g., RF signals) from an external control unit 222. The external control unit 222 can be device that is worn on the skin of the user or can be carried by the user and can have a form similar to a pager or cellular phone, if desired. As another alternative, the external control unit 222 may not be worn or carried by the user but may only be available at, for example, a home station or at a clinician's office.

The signals sent to the processor 232 via the antenna 338 and receiver 230 can be used to modify or otherwise direct the operation of the implantable pulse generator. For example, the signals may be used to modify the pulses of the implantable pulse generator such as modifying one or more of pulse duration, pulse frequency, pulse waveform, and pulse strength. The signals may also direct the implantable pulse generator to cease operation or to start operation or to start charging the battery. Additionally or alternatively, the implantable pulse generator can include a port into which a lead to the external control unit can be plugged so that information, control signals, or the like can be transmitted or received through a wired connection.

Optionally, the implantable pulse generator may include a transmitter, with or without a receiver, coupled to the processor and antenna for transmitting signals to the external control unit 222 or another unit capable of receiving the signals. For example, the implantable pulse generator may transmit signals indicating whether the implantable pulse generator is operating properly or not or indicating when the battery needs to be charged. The processor may also be capable of transmitting information about the pulse characteristics so that a user or clinician can determine or verify the characteristics. In some embodiments, the implantable pulse generator can send back signals to the external control unit from any recording electrodes 106 on the lead 102. Such signals may be used to monitor the stimulation treatment, to verify that the lead is still correctly positioned, or to assist in the implantation procedure.

The implantable pulse generator may include information storage capacity. This can be used to store pulse parameters and the like, as well as information that can be later transmitted to the external control unit 222.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A method for brain stimulation, the method comprising:
    inserting a lead into a cranium of a patient, the lead comprising at least one stimulation electrode disposed along a longitudinal surface of the lead; and at least one recording electrode, separate from the at least one stimulation electrode, disposed on the lead;
    inserting a stylet into the lead to assist in inserting the lead into the cranium of the patient;
    identifying target neurons using the at least one recording electrode;
    rotating the stylet to rotate the lead and assist in identifying the target neurons;
    implanting a pulse generator in the patient; and
    stimulating the target neurons using the at least one stimulation electrode and the implanted pulse generator.

2. The method of claim 1, wherein implanting a pulse generator comprises implanting the pulse generator in a burr hole in a skull of the patient.

3. The method of claim 1, further comprising receiving signals at the implanted pulse generator from an external source.

4. The method of claim 3, further comprising transmitting signals from the implanted pulse generator to an external receiver.

5. The method of claim 1, further comprising operating the at least one recording electrode using the implanted pulse generator.

6. The method of claim 5, wherein operating the at least one recording electrode comprises operating the at least one recording electrode after stimulating the target neurons with the at least one stimulation electrode.

7. The method of claim 6, further comprising analyzing signals from the at least one recording electrode after stimulating the target neurons with the at least one stimulation electrode.

8. The method of claim 1, wherein the lumen is a stylet lumen and the lumen comprises a non-circular lateral cross-section comprising a plurality of arms extending from a central cavity.

9. The method of claim 1, wherein the lead comprises a plurality of stimulation electrodes disposed along the longitudinal surface of the lead; and wherein at least one of the at least one recording electrodes is disposed between two of the plurality of stimulation electrodes.

10. The method of claim 1, wherein the at least one recording electrode comprises one or more sets of recording electrodes disposed at intervals around the circumference of the lead at a same longitudinal position along the lead.

11. The method of claim 10, wherein at least one of the sets of recording electrodes comprises four recording electrodes disposed around the circumference of the lead at 90° intervals.

12. The method of claim 8, wherein the stylet has a lateral cross-section corresponding to the lateral cross-section of the stylet lumen.

13. A method for brain stimulation, the method comprising:
    inserting a stylet into a lead to assist in inserting the lead into a cranium of a patient, the lead comprising a plurality of stimulation electrodes disposed along a longitudinal surface of the lead; and at least one recording electrode, separate from the plurality of stimulation electrodes, disposed along the longitudinal surface of the lead, wherein at least one of the at least one recording electrodes is disposed between two of the plurality of stimulation electrodes, wherein the lead defines a lumen having a non-circular lateral cross-section extending longitudinally through at least a portion of the lead and the stylet has a corresponding lateral cross-section;
    inserting the lead and stylet into the cranium of the patient;
    identifying target neurons using the at least one recording electrode;
    stimulating the target neurons using at least one of the plurality of stimulation electrodes; and
    rotating the lead using the stylet, after identifying the target neurons, to align at least one of the plurality of stimulation electrodes with the target neurons.

14. The method of claim 13, wherein the lumen has a lateral cross-section comprising a plurality of arms extending from a central cavity.

15. The method of claim 14, wherein the lumen has a cruciform or star-shaped lateral cross-section.

16. The method of claim 13, wherein a one of the plurality of stimulation electrodes circumferentially surrounds a one of the at least one recording electrode, wherein the recording electrode and stimulation electrode are separated by a non-conductive region.

17. The method of claim 13, wherein each recording electrode consists essentially of an exposed tip of a wire.

18. The method of claim 13, wherein the at least one recording electrode comprises one or more sets of recording electrodes disposed at intervals around the circumference of the lead at a same longitudinal position along the lead.

19. The method of claim 18, wherein the at least one of the sets of recording electrodes comprises four recording electrodes disposed around the circumference of the lead at 90° intervals.

20. A method for brain stimulation, the method comprising:
- inserting a lead into a cranium of a patient, the lead comprising at least one stimulation electrode disposed along a longitudinal surface of the lead; and at least one recording electrode, separate from the at least one stimulation electrode, disposed on the lead;
- inserting a stylet into the lead to assist in inserting the lead into the cranium of the patient;
- identifying target neurons using the at least one recording electrode;
- rotating the stylet to rotate the lead and assist in identifying the target neurons;
- implanting a pulse generator in the patient; and
- stimulating the target neurons using the at least one stimulation electrode and the implanted pulse generator, wherein each recording electrode consists essentially of an exposed tip of a wire.

21. The method of claim 20, wherein a one of the stimulation electrodes circumferentially surrounds a one of the at least one recording electrode, wherein the recording electrode and stimulation electrode are separated by a non-conductive region.

* * * * *